United States Patent [19]

Cunkle et al.

[11] Patent Number: 5,928,558
[45] Date of Patent: Jul. 27, 1999

[54] DERIVATIVES OF 1-OXYL-4-AMINO-2,2,6,6-TETRAMETHYLPIPERIDINE AS POLYMERIZATION INHIBITORS FOR (METH)ACRYLATE MONOMERS

[75] Inventors: Glen T. Cunkle, Stamford; Matthew E. Gande, Danbury, both of Conn.; Raymond Seltzer, New City, N.Y.

[73] Assignee: Ciba Specialty Chemicals Corporation, Tarrytown, N.Y.

[21] Appl. No.: 09/065,271

[22] Filed: Apr. 23, 1998

Related U.S. Application Data

[63] Continuation-in-part of application No. 08/876,015, Jun. 13, 1997.

[51] Int. Cl.$^6$ ............................ C09K 3/00; C07D 211/58
[52] U.S. Cl. .................... 252/182.18; 546/244; 546/208; 540/485; 526/83
[58] Field of Search .............................. 526/83; 546/244, 546/208; 540/485; 252/182.18

[56] References Cited

U.S. PATENT DOCUMENTS

| | | | |
|---|---|---|---|
| 3,474,988 | 10/1969 | Bailey | 244/536 |
| 3,488,388 | 1/1970 | Altiucker | 564/168 |
| 5,545,782 | 8/1996 | Winter et al. | 585/5 |

FOREIGN PATENT DOCUMENTS

| | | |
|---|---|---|
| 810 196 | 12/1997 | European Pat. Off. . |
| 19510184 | 9/1996 | Germany . |
| 6036501 | 2/1985 | Japan . |
| 1127127 | 9/1968 | United Kingdom . |

*Primary Examiner*—Alan L. Rotman
*Assistant Examiner*—Charanjit S. Aulakh
*Attorney, Agent, or Firm*—Luther A. R. Hall

[57] ABSTRACT

Selected derivatives of 1-oxyl-2,2,6,6-tetramethyl-4-aminopiperidine are surprisingly effective as inhibitors to prevent the premature polymerization of acrylic and methacrylic acids, their esters, their amides, vinyl acetate and acrylonitrile in the presence of water.

37 Claims, No Drawings

DERIVATIVES OF 1-OXYL-4-AMINO-2,2,6,6-TETRAMETHYLPIPERIDINE AS POLYMERIZATION INHIBITORS FOR (METH)ACRYLATE MONOMERS

This is a continuation-in-part of application Ser. No. 08/876,015, filed on Jun. 13, 1997.

The instant invention pertains to the use of selected derivatives of 1-oxyl-2,2,6,6-tetramethyl-4-aminopiperidine as inhibitors for preventing the premature polymerization of acrylic and methacrylic acids, their esters and amides, of vinyl acetate and of acrylonitrile in the presence of water.

BACKGROUND OF THE INVENTION

Many of the industrially important ethylenically unsaturated monomers are highly susceptible to unwanted radical polymerization initiated either thermally or by adventitious impurities. Some examples of these monomers are acrylic and methacrylic acid, acrylate and methacrylate esters, acrylamide and methacrylamide, vinyl acetate and acrylonitrile. Premature polymerization may occur during manufacture, purification or storage of the monomer. Many of these monomers are purified by distillation. It is in this operation where premature polymerization is most likely to occur and to be the most troublesome. Methods to prevent or reduce the amount of such polymerization are thus highly desirable since the prevention or mitigation of such premature polymerization increases the yield of purified monomer and also insures against costly and potentially dangerous runaway polymerization in the plant.

Stable nitroxides are known in the art to be effective in preventing the premature radical polymerization of ethylenically unsaturated monomers. Some examples are seen in U.S. Pat. No. 3,747,988 in the stabilization of acrylonitrile. U.S. Pat. No. 3,488,338 describes the stabilization of chloroprene. British Patent No. 1,127,127 describes the stabilization of acrylic acid; and Japanese Sho 60-36501 describes the stabilization of acrylate and methacrylate esters. There is no mention of derivatives of 4-amino-2,2,6,6-tetramethylpiperidine-1-oxyl in these references.

German Application DE 195 10 184 A1 describes amide and formamide derivatives of 1-oxyl-2,2,6,6-tetramethyl-4-aminopiperidine as stabilizers for radically polymerizable monomers, but does not differentiate between aqueous and non-aqueous systems.

U.S. Pat. No. 5,545,786 describes the use of selected nitroxide compounds in the prevention of the premature polymerization of vinyl aromatic monomers such as styrene especially in the presence of oxygen. There is no disclosure or suggestion that such nitroxide compounds would be particularly effective in stabilizing acrylic monomers, such as acids, esters or amides, or vinyl acetate or acrylonitrile especially in the presence of water.

U.S. Pat. No. 5,254,760 discloses the use of selected nitroxide compounds in combination with an aromatic nitro compound for stabilizing vinyl aromatic monomers such as styrene. Again, there is no mention of aliphatic vinyl compounds or of the especial effectiveness of some selected nitroxide compounds in preventing the premature polymerization of such aliphatic vinyl monomers in the presence of water.

EP 697,386 generically discloses the use of selected nitroxyl compounds for preventing the premature polymerization of aromatic vinyl monomers such as styrene or aliphatic vinyl monomers such as acrylic monomers. Specifically, this reference teaches that 1-oxyl-4-acetylamino-2,2,6,6-tetramethylpiperidine alone or in combination with p-nitrosophenol or 2-methyl-4-nitrosophenol is effective in stabilizing styrene from premature polymerization. There is no mention that 1-oxyl-4-acetylamino-2,2,6,6-tetramethylpiperidine is used with an aliphatic vinyl monomer alone, and certainly no suggestion that said 1-oxyl-4-acetylamino-2,2,6,6-tetramethylpiperidine would be particularly effective with such aliphatic vinyl monomers in the presence of water.

EP 810,196 discloses the use inter alia of 1-oxyl-2,2,6,6-tetramethyl-4-acetylaminopiperidine in combination with a phosphine, such as triphenylphosphine, or a cobalt compound, such as cobalt acetate, as inhibitors to prevent the polymerization of (meth)acrylic acid or esters thereof. There is no teaching that 1-oxyl-2,2,6,6-tetramethyl-4-acetylaminopiperidine alone would be efficacious for that purpose.

Since, during the processes to produce and purify various ethylenically unsaturated monomers, water is often present during one of the process steps, there is a long felt need for the stable nitroxide inhibitor to be sufficiently water soluble or miscible to remain homogeneous in wet monomer streams and to prevent polymerization in the aqueous phase and yet for the inhibitor to be able to partition to such an extent that it can prevent polymerization in both the aqueous phase and in the organic monomer phase for inhibition protection throughout the entire process.

OBJECT OF THE INVENTION

The object of this invention is to provide a derivative of 1-oxyl-2,2,6,6-tetramethyl-4-aminopiperidine of sufficient water solubility and the concomitant ability to partition into an organic phase which will prevent the premature polymerization of ethylenically unsaturated monomers in the presence of water.

DETAILED DESCRIPTION

The instant invention is to a monomer composition stabilized against premature polymerization in the presence of water which comprises (A) an ethylenically unsaturated monomer which is an unsaturated acid, an unsaturated ester, an unsaturated amide, an unsaturated nitrile, unsaturated ether, vinyl pyridine, diethyl vinylphosphonate or sodium styrenesulfonate, and (B) an effective stabilizing amount of a compound of formula I

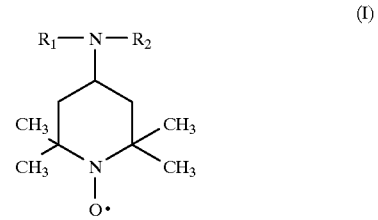

wherein $R_1$ is hydrogen, alkyl of 1 to 4 carbon atoms, or said alkyl substituted by one or two hydroxyl, interrupted by one or two oxygen atoms, or both substituted by one hydroxyl and interrupted by one or two oxygen atoms, $R_2$ is —CO—$R_3$ where $R_3$ has the same meaning as $R_1$, or $R_3$ is —NH$R_4$ wherein $R_4$ is alkyl of 1 to 4 carbon atoms, said alkyl substituted by one or two hydroxyl, substituted by alkoxy of 1 to 2 carbon atoms, or said alkyl both substituted by one hydroxyl and by one alkoxy of 1 to 2 carbon atoms, or $R_1$ and $R_2$ together are —CO—$CH_2CH_2$—CO—, —CO—CH=CH—CO— or —$(CH_2)_6$—CO—; and with the proviso that, when $R_3$ is alkyl of 1 to 4 carbon atoms, $R_1$ is not hydrogen.

Preferably, $R_1$ is hydrogen or n-butyl.

Preferably $R_2$ is —CO—$R_3$ where $R_3$ is hydrogen, methyl, ethyl, n-propyl, isopropyl, methoxymethyl or 2-methoxyethoxymethyl; or $R_2$ is N-butylcarbamoyl.

The amount of water present in the instant composition ranges from 0.1% to 99% by weight of the total composition.

The monomers of component (A) have at least one carbon—carbon double bond capable of undergoing free radical induced polymerization. Such monomers are well-known in commerce and comprise a wide variety of structural types. Typical examples of such monomers are the unsaturated acids such as acrylic acid, methacrylic acid and crotonic acid; unsaturated esters such as the acrylates and methacrylates exemplified by butyl acrylate, methyl methacrylate, ethyl acrylate, methyl acrylate and vinyl acetate; unsaturated amides such as acrylamide and methacrylamide; unsaturated nitriles such as acrylonitrile and methacrylonitrile; unsaturated ethers such as methyl vinyl ether; and miscellaneous vinyl monomers such as the vinyl pyridines, diethyl vinylphosphonate and sodium styrenesulfonate.

Preferably the monomer is acrylic acid, methacrylic acid, butyl acrylate, ethyl acrylate, methyl methacrylate, vinyl acetate, acrylamide or acrylonitrile; most preferably acrylic acid, vinyl acetate or acrylonitrile; most especially acrylic acid.

The effective stabilizing amount of component (B) is 1 to 10000 ppm by weight based on the weight of monomer of component (A). Preferably, the amount of component (B) is 1 to 2000 ppm by weight based on the monomer of component (A). Most preferably, the amount of component (B) is 1 to 1000 ppm by weight based on the monomer of component (A).

The instant invention also relates to some new compounds of formula II

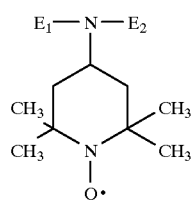

(II)

wherein $E_1$ is hydrogen or alkyl of 1 to 4 carbon atoms, and $E_2$ is —CO-$E_3$ where $E_3$ is alkyl of 1 to 4 carbon atoms which alkyl is interrupted by one or two oxygen atoms, or $E_3$ is —$NHE_4$ where $E_4$ is alkyl of 1 to 4 carbon atoms.

Preferably, $E_1$ is hydrogen or butyl; most preferably hydrogen.

Preferably, $E_3$ is methoxymethyl or 2-methoxyethoxymethyl; or $E_2$ is N-butylcarbamoyl.

The instant invention also pertains to a process for preventing the premature polymerization of an unsaturated monomer in the presence of water by incorporating therein an effective stabilizing amount of a compound of formula I described above.

The polymerization inhibitor amide can be introduced into the monomer to be protected by any conventional method. It may be added just upstream of the point of desired application by any suitable means. In addition, this mixture may be injected separately into the distillation train along with the incoming feed of monomer or through separate entry points providing efficient distribution of the activated inhibitor mixture. Since the inhibitor is gradually depleted during operation, it is generally necessary to maintain the appropriate amount of the inhibitor amide in the distillation system by adding additional inhibitor during the course of the distillation process. Such addition may be carried out either on a continuous basis or by intermittently charging fresh inhibitor into the distillation system if the concentration of the inhibitor is to be maintained above the minimum required level.

The nitroxide amides of this invention are highly water compatible. As many of the processes needed to produce and purify the various ethylenically unsaturated monomers may have some water present during one of the process steps, it is important that the instant stable nitroxide amide inhibitor be sufficiently water soluble to prevent polymerization in the aqueous phase and yet for the inhibitor to be able to partition significantly into the organic monomer phase for inhibition protection throughout the entire process. Undesired premature polymerization must be limited or mitigated throughout the purification process to insure that the reactors, tanks and pipes used to make, store and transport the purified monomer remain free from high molecular weight polymeric material. The instant amide inhibitors are tailored to have the desirable water compatibility properties needed to bring this about.

The amount of water present will depend on the specific monomer being stabilized. In the case of monomers of limited compatibility with water such as butyl acrylate, the water content will depend on the amount needed to saturate the monomer, only a few percent. On the other hand with water miscible monomers such as acrylic acid, the amount of water possible is theoretically much higher.

The following examples are meant to illustrate the instant invention and are not to be construed to limit the scope of the instant invention in any manner whatsoever.

EXAMPLE 1

N-(1-Oxyl-2,2,6,6-tetramethylpiperidin-4-yl) formamide

The title compound is prepared according to the procedure of E. J. Vlietstra et al., Macromolecules, 1990, 23, 946.

EXAMPLE 2

N-(1-Oxyl-2,2,6,6-tetramethylpiperidin-4-yl) octanamide

To a stirred 0° C. solution of 1.0 g of 1-oxyl-4-amino-2,2,6,6-tetramethylpiperidine and 0.65 g of triethylamine in 10 mL of methylene chloride is added dropwise a solution of 0.95 g of octanoyl chloride in 5 mL of methylene chloride. After the addition is complete, the reaction mixture is allowed to warm to ambient temperature. After two more hours, the reaction mixture is washed with 1% aqueous sodium hydroxide and finally water. The organic phase is dried over anhydrous magnesium sulfate, filtered and concentrated. The title compound is isolated as a red oil after column chromatography.

EXAMPLE 3

N-(1-Oxyl-2,2,6,6-tetramethylpiperidin-4-yl) methoxyacetamide

The title compound is synthesized using the same general procedure as described in Example 2 and using methoxyacetyl chloride in place of octanoyl chloride. The title compound is isolated as an orange solid after column chromatography and melts at 124–125° C.

EXAMPLE 4

N-(1-Oxyl-2,2,6,6-tetramethylpiperidin-4-yl)-2-methoxyethoxyacetamide

The title compound is synthesized using the same general procedure as described in Example 2 and using methoxyethoxyacetyl chloride in place of octanoyl chloride. The title compound is isolated as a red oil after column chromatography.

EXAMPLE 5

1-Butyl-3-(1-oxyl-2,2,6,6-tetramethylpiperidin-4-yl) urea

To a stirred solution of 1.0 g of 1-oxyl-4-amino-2,2,6,6-tetramethylpiperidine in 75 mL of dry toluene is added dropwise 0.65 mL of butyl isocyanate. The reaction mixture is stirred for 16 hours. The solution is then concentrated to yield the title compound as a red oil.

EXAMPLE 6

N-Butyl-N-(1-oxyl-2,2,6,6-tetramethylpiperidin-4-yl)formamide

A pressure reactor is charged with 10 g of 4-butylamino-2,2,6,6-piperidine and 100 mL of ethyl formate and then purged with nitrogen. The reactor is immersed in an 100° C. oil bath for three hours. A maximum pressure of 24 psi is observed. The resultant ethanol and unreacted ethyl formate are distilled off under vacuum.

The intermediate N-formyl amine product is then oxidized to corresponding nitroxide as seen below.

To a refluxing solution of the 20 g of the intermediate N-formyl amine and 0.3 g of molybdenum trioxide in 200 mL of methylene chloride is added 60 mL of 70% aqueous tert-butyl hydroperoxide in 10 mL portions over a six hour period. The molybdenum catalyst is then removed by filtration. The filtrate is washed with water, dried over anhydrous magnesium sulfate, filtered and concentrated to yield the title compound as an orange solid which melts at 77–79° C.

EXAMPLE 7

N-Butyl-N-(1-oxyl-2,2,6,6-tetramethylpiperidin-4-yl)acetamide

To a stirred solution of 95 g of 4-butylamino-2,2,6,6-tetramethylpiperidine in 500 mL of diethyl ether is added dropwise 50 mL of acetic anhydride. After the addition is complete, the reaction mixture is stirred at 0° C. for one hour and then at 20° C. for three hours. The resulting precipitate is collected by filtration and washed with diethyl ether till all the orange color is removed. The free amine intermediate is isolated by partitioning the solid between aqueous sodium hydroxide and ether.

The intermediate N-acetyl amine product is then oxidized to the corresponding nitroxide as follows:

To a stirred 50° C. solution of 13.3 g of N-butyl-N-(2,2,6,6-tetramethylpiperidin-4-yl)acetamide, 0.075 g of sodium tungstate-dihydrate and 0.075 g of ethylenediaminetetraacetic acid in 25 mL of methanol is added 35 mL of 30% aqueous hydrogen peroxide over a three hour period. After the addition is complete, the reaction mixture is stirred another two hours. The reaction mixture is then partitioned between diethyl ether and water. The organic phase is washed with water, 1% aqueous hydrogen chloride and then water. After drying over anhydrous magnesium sulfate and concentrating, the title compound is obtained as a red solid. After crystallization from hexane, the compound melts at 84–85° C.

EXAMPLE 8

N-(1-Oxyl-2,2,6,6-tetramethylpiperidin-4-yl) caprolactam

This compound is prepared by the method of Example 14 of U.S. Pat. No. 4,472,547.

In the Examples two different test methods are employed to determine the effectiveness of the nitroxide amides as inhibitors. The method is chosen to simulate different aspects of the purification processes.

METHOD 1

Acrylic acid is distilled to remove any storage stabilizer present. Stock stabilizer solutions (1.5 mg/mL) are prepared in propionic acid. This stock solution is added to the distilled acrylic acid to give a test solution having 5 ppm of total stabilizer. Aliquots of this test solution are then placed into three separate reaction tubes. Each tube is purged with a gas mixture (0.65% oxygen in nitrogen) for ten minutes. The tubes are then sealed and placed in a 110° C. oil bath. The tubes are watched till the appearance of visible polymer formation is observed as a precipitate. Failure times are reported as an average of at least three tubes.

METHOD 2

Test solutions are prepared as in Method 1 except that the stock stabilizer solution is prepared at 0.75 mg/mL, yielding 2.5 ppm total stabilizer in the test solution. Aliquots (1 mL) of the test solution are placed into three separate reaction tubes. To each tube is added 0.5 mL of toluene and 0.5 mL of distilled water. Each tube is purged as described in Method 1 and then sealed. The tubes are placed in a 90° C. oil bath and heated till visible polymer is observed as a precipitate. Failure times are reported as an average of at least three tubes.

EXAMPLE 9

Following the procedure of Method 1, it is seen that water miscible nitroxides and hydrophobic nitroxides each perform similarly in neat acrylic acid in the absence of water.

TABLE 1

Stabilization of Neat Acrylic Acid

| Compound* of Example (5 ppm by weight) | Time to Onset of Polymerization (minutes) |
| --- | --- |
| none | 8 |
| A | 147 |
| Example 3 | 165 |
| Example 6 | 109 |

*A is bis(1-oxyl-2,2,6,6-tetramethylpiperidin-4-yl) sebacate.

Each of the nitroxide compounds provide nearly the same stabilization efficacy to neat acrylic acid.

EXAMPLE 10

Following the procedure of Method 2 where water is present in the acrylic acid, there is a clear difference in the superior stabilization performance of the instant water compatible nitroxides of formula I compared to the hydrophobic nitroxides as seen in Table 2.

TABLE 2

Stabilization of Aqueous Acrylic Acid

| Compound* of Example (2.5 ppm by weight) | Time to Onset of Polymerization (minutes) |
| --- | --- |
| none | 29 |
| A | 241 |
| Example 1 | 498 |
| Example 2 | 280 |
| Example 3 | 418 |
| Example 6 | 503 |

*A is bis(1-oxyl-2,2,6,6-tetramethylpiperidin-4-yl) sebacate.

EXAMPLE 11

Following the procedure of Method 2 where water is present in the acrylic acid, there is a clear difference in the superior stabilization performance of the instant water compatible nitroxides of formula I compared to the hydrophobic nitroxide B as seen in Table 3.

TABLE 3

Stabilization of Aqueous Acrylic Acid

| Compound* of Example (2.5 ppm by weight) | Time to Onset of Polymerization (minutes) |
| --- | --- |
| none | 30 |
| B | 70 |
| Example 8 | 365 |
| Example 6 | 500 |

*B is N-(1-oxyl-2,2,6,6-tetramethylpiperidin-4-yl)dodecylsuccinimide.

What is claimed is:

1. A monomer composition stabilized against premature polymerization in the presence of water which comprises
   (A) an ethylenically unsaturated monomer which is an unsaturated acid, an unsaturated ester, an unsaturated amide, an unsaturated nitrile, unsaturated ether, vinyl pyridine, diethyl vinylphosphonate or sodium styrenesulfonate, and
   (B) an effective stabilizing amount of a compound of formula I

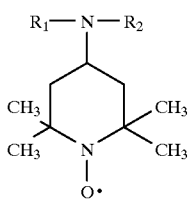

(I)

wherein
   $R_1$ is hydrogen, alkyl of 1 to 4 carbon atoms, or said alkyl substituted by one or two hydroxyl, interrupted by one or two oxygen atoms, or both substituted by one hydroxyl and interrupted by one or two oxygen atoms,
   $R_2$ is —CO—$R_3$ where $R_3$ has the same meaning as $R_1$, or $R_3$ is —NH$R_4$ wherein $R_4$ is alkyl of 1 to 4 carbon atoms, said alkyl substituted by one or two hydroxyl, substituted by alkoxy of 1 to 2 carbon atoms, or said alkyl both substituted by one hydroxyl and by one alkoxy of 1 to 2 carbon atoms, or
   $R_1$ and $R_2$ together are —CO—CH$_2$CH$_2$—CO—, —CO—CH═CH—CO— or —(CH$_2$)$_6$—CO—;
and
   with the proviso that, when $R_3$ is alkyl of 1 to 4 carbon atoms, $R_1$ is not hydrogen.

2. A composition according to claim 1 where in the compound of formula I, $R_1$ is hydrogen or n-butyl.

3. A composition according to claim 1 where in the compound of formula I, $R_2$ is —CO—$R_3$ where $R_3$ is hydrogen, methyl, ethyl, n-propyl, isopropyl, methoxymethyl or 2-methoxyethoxymethyl; or $R_2$ is N-butylcarbamoyl.

4. A composition according to claim 1 wherein the amount of water is from 0.1% to 99% by weight based on the total composition.

5. A composition according to claim 1 wherein the monomer of component (A) is an unsaturated acid, an unsaturated ester, an unsaturated amide, an unsaturated nitrile, an unsaturated ether or vinyl compound.

6. A composition according to claim 5 wherein the unsaturated monomer is acrylic acid, methacrylic acid, an ester of acrylic acid or methacrylic acid, an amide of acrylic acid or methacrylic acid, vinyl acetate or acrylonitrile.

7. A composition according to claim 6 wherein the unsaturated monomer is acrylic acid, methacrylic acid, butyl acrylate, ethyl acrylate, methyl methacrylate, vinyl acetate, acrylamide or acrylonitrile.

8. A composition according to claim 7 wherein the monomer is acrylic acid, vinyl acetate or acrylonitrile.

9. A composition according to claim 8 wherein the monomer is acrylic acid.

10. A composition according to claim 1 wherein the effective stabilizing amount of component (B) is 1 to 10000 ppm by weight based on the weight of monomer of component (A).

11. A composition according to claim 10 wherein the effective stabilizing amount of component (B) is 1 to 2000 ppm by weight based on the monomer of component (A).

12. A composition according to claim 11 wherein the effective stabilizing amount of component (B) is 1 to 1000 ppm by weight based on the monomer of component (A).

13. A composition according to claim 1 wherein the compound of formula I is
   (a) N-(1-oxyl-2,2,6,6-tetramethylpiperidin-4-yl)formamide,
   (b) N-(1-oxyl-2,2,6,6-tetramethylpiperidin-4-yl)methoxyacetamide,
   (c) N-(1-oxyl-2,2,6,6-tetramethylpiperidin-4-yl)-2-methoxyethoxyacetamide,
   (d) 1-butyl-3-(1-oxyl-2,2,6,6-tetramethylpiperidin-4-yl)urea,
   (e) N-butyl-N-(1-oxyl-2,2,6,6-tetramethylpiperidin-4-yl)formamide,
   (f) N-butyl-N-(1-oxyl-2,2,6,6-tetramethylpiperidin-4-yl)acetamide,
   (g) N-(1-oxyl-2,2,6,6-tetramethylpiperidin-4-yl)succinimide,
   (h) N-(1-oxyl-2,2,6,6-tetramethylpiperidin-4-yl)maleimide, or (i) N-(1-oxyl-2,2,6,6-tetramethylpiperidin-4-yl)caprolactam.

14. A composition according to claim 13 wherein compound of formula I is (a) N-(1-oxyl-2,2,6,6-tetramethylpiperidin-4-yl) formamide,
(b) N-(1-oxyl-2,2,6,6-tetramethylpiperidin-4-yl) methoxyacetamide,
(e) N-butyl-N-(1-oxyl-2,2,6,6-tetramethylpiperidin-4-yl) formamide, or
(f) N-butyl-N-(1-oxyl-2,2,6,6-tetramethylpiperidin-4-yl) acetamide.

15. A composition according to claim 14 wherein the compound of formula I is
(e) N-butyl-N-( 1 -oxyl-2,2,6,6-tetramethylpiperidin-4-yl)formamide.

16. A composition according to claim 1 wherein component (A) is acrylic acid and the compound of formula I is N-butyl-N-(1-oxyl-2,2,6,6-tetramethylpiperidin-4-yl) formamide.

17. A process for preventing the premature polymerization of an ethylenically unsaturated monomer (A) which is an unsaturated acid, an unsaturated ester, an unsaturated amide, an unsaturated nitrile, unsaturated ether, vinyl pyridine, diethyl vinylphosphonate or sodium styrenesulfonate, in the presence of water which comprises incorporating therein an effective stabilizing amount of a compound (B) of formula I

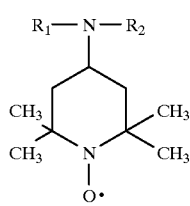
(I)

wherein
$R_1$ is hydrogen, alkyl of 1 to 4 carbon atoms, or said alkyl substituted by one or two hydroxyl, interrupted by one or two oxygen atoms, or both substituted by one hydroxyl and interrupted by one or two oxygen atoms,
$R_2$ is —CO—$R_3$ where $R_3$ has the same meaning as $R_1$, or $R_3$ is —$NHR_4$ wherein $R_4$ is alkyl of 1 to 4 carbon atoms, said alkyl substituted by one or two hydroxyl, substituted by alkoxy of 1 to 2 carbon atoms, or said alkyl both substituted by one hydroxyl and by one alkoxy of 1 to 2 carbon atoms, or
$R_1$ and $R_2$ together are —CO—$CH_2CH_2$—CO—, —CO—CH=CH—CO— or —$(CH_2)_6$—CO—; and
with the proviso that, when $R_3$ is alkyl of 1 to 4 carbon atoms, $R_1$ is not hydrogen.

18. A process according to claim 17 where in the compound of formula I, $R_1$ is hydrogen or n-butyl.

19. A process according to claim 17 where in the compound of formula I, $R_2$ is —CO—$R_3$ where $R_3$ is hydrogen, methyl, ethyl, n-propyl, isopropyl, methoxymethyl or 2-methoxyethoxymethyl; or $R_2$ is N-butylcarbamoyl.

20. A process according to claim 17 wherein the amount of water is 0.1 % to 99% by weight based on the total composition.

21. A process according to claim 17 wherein the monomer of component (A) is an unsaturated acid, an unsaturated ester, an unsaturated amide, an unsaturated nitrile, an unsaturated ether or vinyl compound.

22. A process according to claim 21 wherein the unsaturated monomer is acrylic acid, methacrylic acid, an ester of acrylic acid or methacrylic acid, an amide of acrylic acid or methacrylic acid, vinyl acetate or acrylonitrile.

23. A process according to claim 22 wherein the unsaturated monomer is acrylic acid, methacrylic acid, butyl acrylate, ethyl acrylate, methyl methacrylate, vinyl acetate, acrylamide or acrylonitrile.

24. A process according to claim 23 wherein the monomer is acrylic acid, vinyl acetate or acrylonitrile.

25. A process according to claim 24 wherein the monomer is acrylic acid.

26. A process according to claim 17 wherein the effective stabilizing amount of component (B) is 1 to 10000 ppm by weight based on the weight of monomer of component (A).

27. A process according to claim 26 wherein the effective stabilizing amount of component (B) is 1 to 2000 ppm by weight based on the monomer of component (A).

28. A process according to claim 27 wherein the effective stabilizing amount of component (B) is 1 to 1000 ppm by weight based on the monomer of component (A).

29. A process according to claim 17 wherein the compound of formula I is
(a) N-(1-oxyl-2,2,6,6-tetramethylpiperidin-4-yl) formamide,
(b) N-(1-oxyl-2,2,6,6-tetramethylpiperidin-4-yl) methoxyacetamide,
(c) N-(1-oxyl-2,2,6,6-tetramethylpiperidin-4-yl)-2-methoxyethoxyacetamide,
(d) 1-butyl-3-(1-oxyl-2,2,6,6-tetramethylpiperidin-4-yl) urea,
(e) N-butyl-N-(1-oxyl-2,2,6,6-tetramethylpiperidin-4-yl) formamide,
(f) N-butyl-N-(1-oxyl-2,2,6,6-tetramethylpiperidin-4-yl) acetamide,
(g) N-(1-oxyl-2,2,6,6-tetramethylpiperidin-4-yl) succinimide,
(h) N-(1-oxyl-2,2,6,6-tetramethylpiperidin-4-yl) maleimide, or
(i) N-(1-oxyl-2,2,6,6-tetramethylpiperidin-4-yl) caprolactam.

30. A process according to claim 29 wherein the compound of formula I is
(a) N-(1-oxyl-2,2,6,6-tetramethylpiperidin-4-yl) formamide,
(b) N-(1-oxyl-2,2,6,6-tetramethylpiperidin-4-yl) methoxyacetamide,
(e) N-butyl-N-(1-oxyl-2,2,6,6-tetramethylpiperidin-4-yl) formamide, or
(f) N-butyl-N-(1-oxyl-2,2,6,6-tetramethylpiperidin-4-yl) acetamide.

31. A process according to claim 30 wherein the compound of formula I is
(e) N-butyl-N-(l-oxyl-2,2,6,6-tetramethylpiperidin-4-yl) formamide.

32. A process according to claim 17 wherein component (A) is acrylic acid and the compound of formula I is N-butyl-N-(1-oxyl-2,2,6,6-tetramethylpiperidin-4-yl) formamide.

33. A compound of formula II

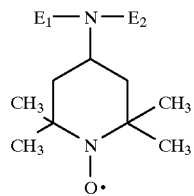

(II)

wherein $E_1$ is hydrogen or alkyl of 1 to 4 carbon atoms, and $E_2$ is —CO-$E_3$ where $E_3$ is alkyl of 1 to 4 carbon atoms which alkyl is interrupted by one or two oxygen atoms, or $E_3$ is —NH$E_4$ where $E_4$ is alkyl of 1 to 4 carbon atoms.

34. A compound according to claim 33 wherein $E_1$ is hydrogen or butyl.

35. A compound according to claim 34 wherein $E_1$ is hydrogen.

36. A compound according to claim 33 wherein $E_3$ is methoxymethyl or 2-methoxyethoxymethyl; or $E_2$ is N-butylcarbamoyl.

37. The compound according to claim 33 which is N-(1-oxyl-2,2,6,6-tetramethylpiperidin-4-yl)methoxyacetamide; N-(1-oxyl-2,2,6,6-tetramethylpiperidin-4-yl)-2-methoxyethoxyacetamide; or 1-butyl-3-(1-oxyl-2,2,6,6-tetramethylpiperidin-4-yl)urea.

* * * * *